United States Patent
Mayer et al.

[11] Patent Number: 5,612,286
[45] Date of Patent: Mar. 18, 1997

[54] HERBICIDAL N-[PYRIMIDIN-2-LY)AMINOCARBONYL]-BENZENESULFONAMIDES

[75] Inventors: Horst Mayer, Ludwigshafen; Gerhard Hamprecht, Weinheim; Karl-Otto Westphalen, Speyer; Matthias Gerber, Limburgerhof; Uwe Kardorff, Mannheim; Helmut Walter, Obrigheim, all of Germany

[73] Assignee: BASF Aktiengesellschaft, Ludwigshafen, Germany

[21] Appl. No.: 290,959

[22] PCT Filed: Feb. 16, 1993

[86] PCT No.: PCT/EP93/00362

§ 371 Date: Aug. 24, 1994

§ 102(e) Date: Aug. 24, 1994

[87] PCT Pub. No.: WO93/16998

PCT Pub. Date: Sep. 2, 1993

[30] Foreign Application Priority Data

Feb. 28, 1992 [DE] Germany .................. 42 06 145.8

[51] Int. Cl.$^6$ ............... C07D 239/47; A01N 43/54
[52] U.S. Cl. ............................ 504/214; 544/321
[58] Field of Search .................... 504/214; 544/321

[56] References Cited

U.S. PATENT DOCUMENTS

| | | | |
|---|---|---|---|
| 4,120,691 | 10/1978 | Levitt | 71/93 |
| 4,169,719 | 10/1979 | Levitt | 71/92 |
| 4,310,346 | 1/1982 | Levitt et al. | 71/92 |
| 4,425,153 | 1/1984 | Adams, Jr. | 71/92 |
| 4,515,624 | 5/1985 | Reap | 71/92 |

FOREIGN PATENT DOCUMENTS

| | | |
|---|---|---|
| 044808 | 1/1982 | European Pat. Off. . |
| 044807 | 1/1982 | European Pat. Off. . |
| 044209 | 1/1982 | European Pat. Off. . |
| 101308 | 2/1984 | European Pat. Off. . |
| 173312 | 8/1985 | European Pat. Off. . |
| 285978 | 10/1988 | European Pat. Off. . |
| 338424 | 10/1989 | European Pat. Off. . |
| 378092 | 7/1990 | European Pat. Off. . |
| 3900172 | 1/1989 | Germany . |

OTHER PUBLICATIONS

Mayer et al., Chemical Abstracts, vol. 118, entry 6988 (1992).
Levitt, Chemical Abstracts, vol. 92, entry 111047 (1979).
Levitt, Chemical Abstracts, vol. 88, entry 6395 (1977).

*Primary Examiner*—John M. Ford
*Attorney, Agent, or Firm*—Keil & Weinkauf

[57] ABSTRACT

N-[(Pyrimidin-2-yl)aminocarbonyl]benzenesulfonamide of the general formula I

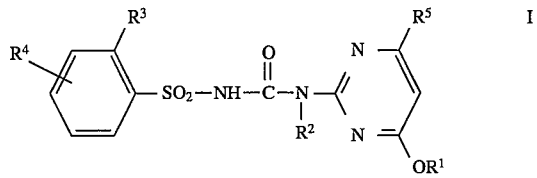

where $R^1$ is methyl or ethyl;

$R^2$ is hydrogen or methyl;

$R^3$ is unsubstituted or substituted alkyl;

a group $ER^6$, in which E is O or S, $R^6$ being unsubstituted or fluorine-substituted alkyl, with the exception of difluoromethoxy, and, if E is O and at the same time $R^5$ is trifluoromethyl, $R^6$ may furthermore be methylsulfonyl, ethylsulfonyl, trifluoromethylsulfonyl, allylsulfonyl or propargylsulfonyl;

$NO_2$ or OH;

dialkylaminosulfonyl if $R^5$ is fluorine;

$C_1$- or $C_2$-alkylsulfonyl which may carry 1 to 3 halogen atoms;

$R^4$ is hydrogen, methyl, ethyl, methoxy, ethoxy, fluorine, chlorine, methylthio, ethylthio or $C_1$ or $C_2$-haloalkoxy; and $R^5$ is fluorine or trifluoromethyl, and their environmentally compatible salts, processes for their preparation and their use.

15 Claims, No Drawings

HERBICIDAL N-[PYRIMIDIN-2-LY) AMINOCARBONYL]-BENZENESULFONAMIDES

This is a 371 of PCT/EP93/00362, filed Feb. 16, 1993.

The present invention relates to N-[(pyrimidin-2-yl)amincarbonyl]benzenesulfonamides of the general formula I

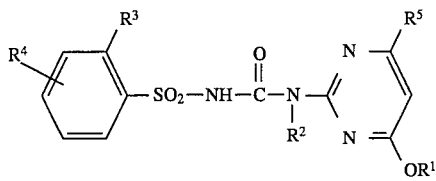

where $R^1$ is methyl or ethyl;

$R^2$ is hydrogen or methyl;

$R^3$ is $C_1$–$C_4$-alkyl which may carry from one to three methoxy groups or fluorine atoms;

a group $ER^6$ in which E is O or S, $R^6$ being $C_1$–$C_2$-alkyl, which may carry from 1 to 3 or 1 to 5 fluorine atoms, with the exception of difluoromethoxy, and, if E is O and at the same time $R^5$ is trifluoromethyl, $R^6$ may furthermore be methylsulfonyl, ethylsulfonyl, trifluoromethylsulfonyl, allylsulfonyl or propargylsulfonyl;

$NO_2$ or OH;

di-$C_1$–$C_3$-alkylaminosulfonyl if $R^5$ is fluorine;

$C_1$- or $C_2$-alkylsulfonyl which may carry 1–3 halogen atoms;

$R^4$ is hydrogen, methyl, ethyl, methoxy, ethoxy, fluorine, chlorine, methylthio, ethylthio or $C_1$–$C_2$-haloalkoxy;

and $R^5$ is fluorine or trifluoromethyl, and their environmentally compatible salts.

The present invention furthermore relates to a process for the preparation of the compounds I and to their use as herbicides.

The prior art includes a number of patents which relate to sulfonylureas having a herbicidal action.

EP-A 44 808 lists the compounds A–D in the form of a table, without further characterization.

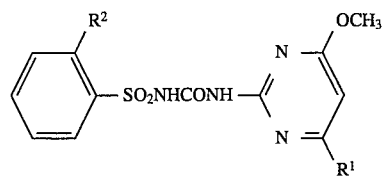

A: $R^1 = CF_3$; $R^2 = OCF_2Cl$
B: $R^1 = F$; $R^2 = OCF_2Cl$
C: $R^1 = CF_3$; $R^2 = OCHF_2$
D: $R^1 = F$; $R^2 = OCHF_2$

The sulfonylurea E is mentioned in EP-A 44 807, likewise without physical characteristics.

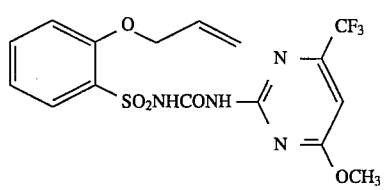

EP-A 338 424 describes methyl benzoates, for example F.

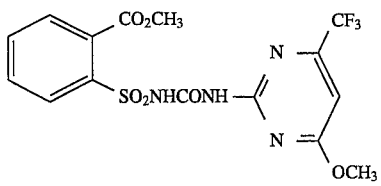

DE-A 39 00 172 relates to benzoates and benzamides and o-halogen-substituted sulfonylureas, for example having the structures G–I.

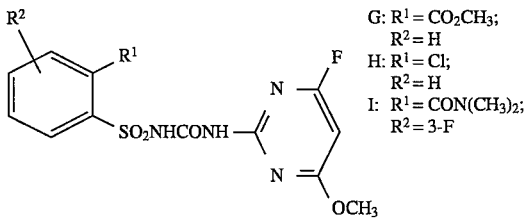

G: $R^1 = CO_2CH_3$; $R^2 = H$
H: $R^1 = Cl$; $R^2 = H$
I: $R^1 = CON(CH_3)_2$; $R^2 = 3$-F

EP-A 101 308 describes higher sulfones, for example J–M.

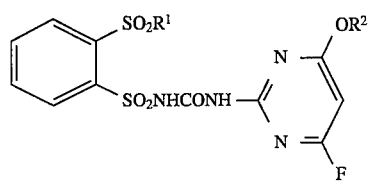

J: $R^1 = n$-$C_3H_7$; $R^2 = CH_3$
K: $R^1 = CH(CH_3)CH_2CH_3$; $R^2 = CH_3$
L: $R^1 = CH_2$—◁; $R^2 = CH_3$
M: $R^1 = C(CH_3)_3$; $R^2 = C_2H_5$

U.S. Pat. No. 4,120,691 (DE-A 27 15 786) mentions the sulfonylureas N and O.

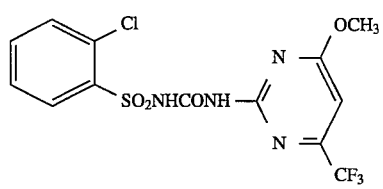

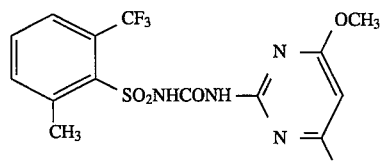

U.S. Pat. No. 4,310,346 discloses sulfonamides having the structure P.

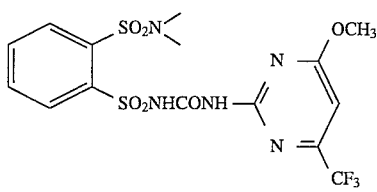

Dimethylcarbamoyl-substituted sulfonylureas having the structure R

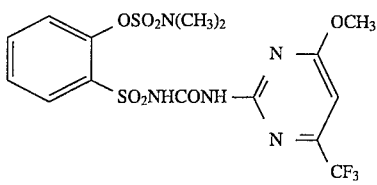

are disclosed in U.S. Pat. No. 4,515,624.

Sulfonylurea derivatives substituted by fluoroalkoxy, sulfamoyl, acyl or alkyl in the ortho position of the phenyl radical are represented by general structural formulae in EP-A 173 312, U.S. Pat. Nos. 4,515,624, 4,425,153 and EP-A 44 209, respectively, without any detailed information on specific structures.

The earlier German Applications P 40 38 430.6 of Dec. 1, 1990 and P 41 05 518.7 of Feb. 22, 1991 describe herbicidal sulfonamides which, compared with the novel compounds, have different substituents in the ortho position of the phenyl radical and/or in the 3/5 positions of the triazine radical.

It is an object of the present invention to synthesize sulfonylureas which have improved properties compared with the known members of this herbicide class.

We have found that this object is achieved by the N-[(pyrimidin-2-yl)aminocarbonyl]benzenesulfonamides of the formula I which are defined at the outset.

In view of their intended use, suitable substituents are, for example, the following radicals:

$R^1$ is methyl or ethyl;

$R^2$ is hydrogen or methyl;

$R^3$ is $C_1$–$C_4$-alkyl, such as methyl, ethyl, n-propyl, isopropyl, n-butyl, isobutyl, sec-butyl or tert-butyl, which may carry from one to three methoxy groups or fluorine atoms;

a group $ER^6$ in which E is O or S, $R^6$ being $C_1$–$C_2$-alkyl, which if $R^6$ is methyl may carry 1 to 3 fluorine atoms and if $R^6$ is ethyl may carry 1 to 5 fluorine atoms, with the exception of difluoromethoxy, and, if E=O and at the same time $R^5$=trifluoromethyl, $R^6$ may furthermore be methylsulfonyl, trifluoromethylsulfonyl, ethylsulfonyl, allylsulfonyl or propargylsulfonyl;

$NO_2$ or OH;

di-($C_1$–$C_3$-alkyl)aminosulfonyl, such as dimethylaminosulfonyl or diethylaminosulfonyl if $R^5$ is fluorine;

$C_1$–$C_2$-alkylsulfonyl, such as methylsulfonyl or ethylsulfonyl, where up to three hydrogen atoms may be replaced by halogen atoms;

$R^4$ is hydrogen, methyl, ethyl, methoxy, ethoxy, fluorine, chlorine, methylthio, ethylthio or $C_1$–$C_2$-haloalkoxy such as trifluoromethoxy or difluoromethoxy; and $R^5$ is fluorine or trifluoromethyl.

Halogen is in general fluorine, chlorine, bromine or iodine, in particular fluorine, chlorine or bromine.

Compounds with $R^1$=methyl and $R^2$=hydrogen are preferred.

Preferred definitions of $R^3$ are: methylsulfonyloxy, trifluoromethyl, trifluoromethoxy, thiomethyl, nitro, methylsulfonyl, ethylsurfonyl, methoxymethyl and N,N-dimethylsulfamoyl.

Particularly preferred compounds I arise as a result of the following combinations of radicals:

a) $R^1$=methyl, $R^2$, $R^4$=H, $R^3$=methylsulfonyloxy, $R^5$=trifluoromethyl;

b) $R^1$=methyl, $R^2$, $R^4$=H, $R^3$=trifluoromethyl, $R^5$=trifluoromethyl or fluorine;

c) $R^1$=methyl, $R^2$, $R^4$=H, $R^3$=trifluoromethoxy, $R^5$=trifluoromethyl or fluorine;

d) $R^1$=methyl, $R^2$=H, $R^3$=thiomethyl or methoxy, $R^4$=6-methylthio, $R^5$=trifluoromethyl or fluorine;

e) $R^1$=methyl, $R^2$, $R^4$=H, $R^3$=methoxymethyl, $R^5$=trifluoromethyl or fluorine;

f) $R^1$=methyl, $R^2$, $R^4$=H, $R^3$=nitro, $R^5$=trifluoromethyl or fluorine;

g) $R^1$=methyl, $R^2$, $R^4$=H, $R^3$=methyl- or ethylsulfonyl, $R^5$=trifluoromethyl or fluorine;

h) $R^1$=methyl, $R^2$, $R^4$=H, $R^3$=N,N-dimethylsulfamoyl, $R^5$=fluorine.

The novel sulfonylureas of the formula I are obtainable by various methods which are described in the literature. Particularly advantageous methods (A–D) are described in detail below by way of example.

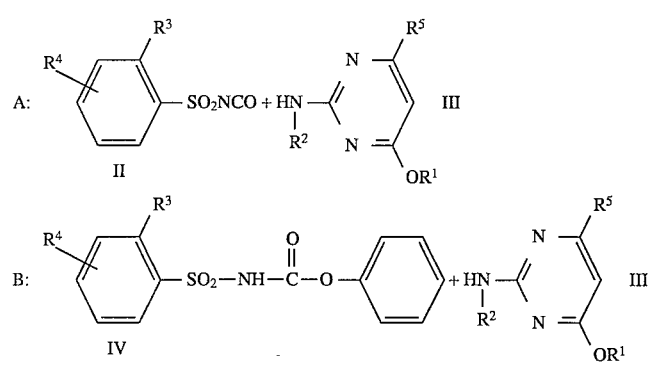

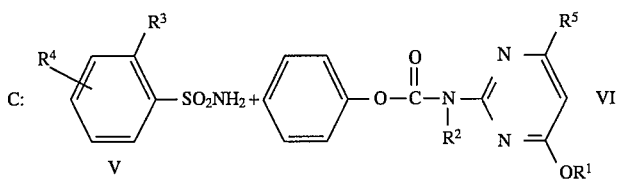
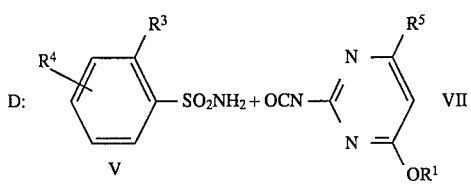
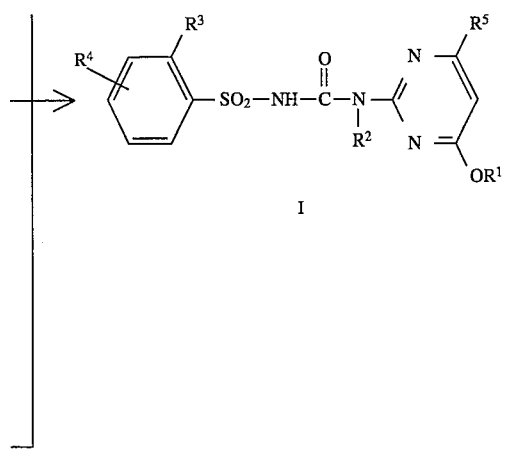

A: A sulfonyl isocyanate II is reacted in a conventional manner (EP-A-162 723) with about the stoichiometric amount of a 2-aminopyrimidine derivative III at from 0° to 120° C., preferably from 10° to 100° C. The reaction can be carried out under atmospheric pressure or superatmospheric pressure (up to 50 bar), preferably at from 1 to 5 bar, continuously or batchwise.

Solvents and diluents which are inert under the particular reaction conditions are advantageously used for the reactions. Examples of suitable solvents are halohydrocarbons, in particular chlorohydrocarbons, e.g. tetrachloroethylene, 1,1,2,2- or 1,1,1,2-tetrachloroethane, dichloropropane, methylene chloride, dichlorobutane, chloroform, chloronaphthalene, dichloronaphthalene, carbon tetrachloride, 1,1,1- or 1,1,2-trichloroethane, trichloroethylene, pentachloroethane, o-, m- or p-difluorobenzene, 1,2-dichloroethane, 1,1-dichloroethane, 1,2-cis-dichloroethylene, chlorobenzene, fluorobenzene, bromobenzene, iodobenzene, o-, m- or p-dichlorobenzene, o-, p- or m-dibromobenzene, o-, m- or p-chlorotoluene or 1,2,4-trichlorobenzene; ethers, e.g. ethyl propyl ether, methyl tert-butyl ether, n-butyl ethyl ether, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxane, thioanisole or β,β'-dichlorodiethyl ether; nitrohydrocarbons, such as nitromethane, nitroethane, nitrobenzene, o-, m- or p-chloronitrobenzene or o-nitrotoluene; nitriles, such as acetonitrile, butyronitrile, isobutyronitrile, benzonitrile or m-chlorobenzonitrile; aliphatic or cycloaliphatic hydrocarbons, e.g. heptane, pinane, nonane, o-, m- or p-cymene, gasoline fractions boiling within a range from 70° to 190° C., cyclohexane, methylcyclohexane, decalin, petroleum ether, hexane, naphtha, 2,2,4-trimethylpentane, 2,2,3-trimethylpentane, 2,3,3-trimethylpentane or octane; esters, e.g. ethyl acetate, ethyl acetoacetate or isobutyl acetate; amides, e.g. formamide, methylformamide or dimethylformamide; ketones, e.g. acetone or methyl ethyl ketone, and corresponding mixtures. The solvent is advantageously used in an amount of from 100 to 2,000, preferably from 200 to 700, % by weight, based on the starting material II.

The compound II required for the reaction is generally used in about equimolar amounts (for example from 80 to 120%, based on the particular starting material III). The starting material III in one of the above-mentioned diluents may be initially taken and the starting material II then added.

However, the process for the preparation of the novel compounds is advantageously carried out by initially taking the starting material II, if necessary in one of the above-mentioned diluents, and then adding the starting material III.

To terminate the reaction, stirring is carried out for a further 20 minutes to 24 hours at from 0° to 120° C., preferably from 10° to 100° C., after the addition of the components.

A tertiary amine, e.g. pyridine, α,β-γ-picoline, 2,4- or 2,6-lutidine, 2,4,6-collidine, p-dimethylaminopyridine, trimethylamine, triethylamine, tri-n-propylamine, 1,4-diaza[2.2.2]bicyclooctane [DABCO] or 1,8-diazabicyclo[5.4.0]undec-7-ene, may advantageously be used as a reaction accelerator, in an amount of from 0.01 to 1 mol per mol of starting material II.

The end product I is isolated from the reaction mixture in a conventional manner, for example by distilling off solvents or directly by filtration under suction. The residue can be washed with water or dilute acid to remove basic impurities. However, the residue can also be dissolved in a water-immiscible solvent and washed in the manner described. The desired end products are obtained here in pure form; if necessary, they can be purified by recrystallization, stirring in an organic solvent which takes up the impurities or chromatography.

This reaction is preferably carried out in acetonitrile, methyl tert-butyl ether, toluene or methylene chloride, in the presence of from 0 to 100, preferably from 0 to 50, molar equivalents of a tertiary amine, such as 1,4-diazabicyclo[2.2.2]octane or triethylamine.

B: A corresponding sulfonyl carbamate of the formula IV is reacted in a conventional manner (EP-A-120 814, EP-A-101 407), in an inert orgahic solvent at from 0° to 120° C., preferably from 10° to 100° C., with a 2-aminopyrimidine derivative III. Bases, such as tertiary amines, may be added here, with the result that the reaction is accelerated and the product quality improved.

Suitable bases for this purpose are, for example, tertiary amines as stated under A, in particular triethylamine or 1,4-diazabicyclo[2.2.2]octane, in an amount of from 0.01 to 1 mol per mol of starting material IV.

Advantageously used solvents are those stated under A.

The solvent is used in an amount of from 100 to 2,000, preferably from 200 to 700, % by weight, based on the starting material IV.

The compound IV required for the reaction is used in general in about equimolar amounts (for example from 0 to 120%, based on the particular starting material III). The starting material IV in one of the abovementioned diluents may be initially taken and the starting material III then added.

However, the starting material III in one of the stated solvents or diluents may also be initially taken and the sulfonyl carbamate IV added.

In both cases, a base may be added as a catalyst before or during the reaction.

The end product I can be obtained from the reaction mixture in a conventional manner, as stated under A.

C: A sulfonamide of the formula V is reacted in a conventional manner (EP-A-141 777 and EP-A-101 670), in an inert organic solvent, with about the stoichiometric amount of a phenyl carbamate VI at from 0° to 120° C., preferably from 20° to 100° C. The reaction can be carried out at atmospheric or superatmospheric pressure (up to 50 bar), preferably at from 1 to 5 bar, continuously or batchwise.

Bases such as tertiary amines, which accelerate the reaction and improve the product quality, may be added here. Suitable bases for this purpose are those stated under A, in particular triethylamine, 2,4,6-collidine, 1,4-diazabicyclo[2.2.2]octane [DABCO] or 1,8-diazabicyclo[5.4.0]undec-7-ene (DBU), in an amount of from 0.01 to 1 mol per mol of starting material V.

Advantageously used solvents or diluents are those stated under A.

The solvent is used in an amount of from 100 to 2,000, preferably from 200 to 700, % by weight, based on the starting material V.

The compound V required for the reaction is used in general in about equimolar amounts (for example from 80 to 120%, based on the particular starting materials VI). The starting material VI in one of the above-mentioned diluents may be initially taken and the starting material V then added.

However, the starting material V in one of the stated solvents may also be initially taken and the carbamate VI then added. In both cases, one of the stated bases may be added as a catalyst before or during the reaction.

To terminate the reaction, stirring is carried out for a further 20 minutes to 24 hours at from 0° to 120° C., preferably from 10° to 100° C., in particular from 20° to 80° C., after the addition of the components The sulfonylureas of the formula I are isolated from the reaction mixture by conventional methods as described under A.

D: A sulfonamide of the formula V is reacted in a conventional manner (EP-A-234 352), in an inert organic solvent, with about the stoichiometric amount of an isocyanate VII at from 0° to 150° C., preferably from 10° to 100° C. The reaction can be carried out under atmospheric or superatmospheric pressure (up to 50 bar), preferably at from 1 to 5 bar, continuously or batchwise.

Bases such as tertiary amines, which accelerate the reaction and improve the product quality, may be added before or during the reaction. Suitable bases for this purpose are those stated under A, in particular triethylamine or 2,4,6-collidine, in an amount of from 0.01 to 1 mol per mol of starting material V.

Advantageously used solvents are those stated under A. The solvent is used in an amount of from 100 to 2,000, preferably from 200 to 700, % by weight, based on the starting material V.

The compound V required for the reaction is used in general in about equimolar amounts (for example from 80 to 120%, based on the starting materials VII). The starting material VII in one of the stated diluents may be initially taken and the starting material V then added. However, the sulfonamide may also be initially taken and the isocyanate VII then added.

To terminate the reaction, stirring is carried out for a further 20 minutes to 24 hours at from 0° to 120° C., preferably from 10° to 100° C., in particular from 20° to 80° C., after the addition of the components. The end product I can be obtained from the reaction mixture in the conventional manner, as described under A.

The sulfonyl isocyanates of the formula II which are required as starting materials can be obtained in a conventional manner from the corresponding sulfonamides by phosgenation (Houben-Weyl 11/2 (1985) 1106, U.S. Pat. No. 4,379,769) or by reacting the sulfonamides with chlorosulfonyl isocyanate (German Laid-Open Application DOS 3,132,944).

The sulfonamides of the formula V can be obtained by reacting the corresponding sulfonyl chlorides with ammonia (M. Quaedvlieg in Houben-Weyl, Methoden der organischen Chemie, Georg Thieme Verlag, Stuttgart, 9 (1955), 398–400, F. Muth, ibid., 605 et seq.). However, it is also possible for an o-halobenzenesulfonamide to be subjected to a nucleophilic substitution reaction, for example with an alcohol or thiol, and, for example, for the resulting corresponding thioether to be oxidized to the sulfoxide or sulfone (cf. process examples).

The corresponding sulfonyl chlorides for preparation of the sulfonamides of the formula V are obtained in general by a Meerwein reaction (diazotization of suitable amides and sulfochlorination with sulfur dioxide under catalysis by a copper salt: F. Muth in Houben-Weyl, Methoden der organischen Chemie, Georg Thieme Verlag, Stuttgart, 9 (1955), 579, S. Pawlenko in Houben-Weyl, Methoden der organischen Chemie, Georg Thieme Verlag, Stuttgart, Vol. E 11/2 (1985), 1069), from the corresponding sulfonic acids (F. Muth in Houben-Weyl, Methoden der organischen Chemie, Georg Thieme Verlag, Stuttgart, 9 (1955), 564), by chlorosulfonation of suitable aromatic intermediates (F. Muth, ibid., page 572) or by oxidative chlorination of low-valence sulfur intermediates (mercaptans, diaryl disulfides or S-benzylmercaptans) (F. Muth, ibid., page 580, S. Pawlenko, loc. cit., page 1073).

The sulfonyl carbamates of the formula IV were prepared by conventional reactions or similarly to such reactions (for example EP-A 120 814). However, the sulfonylisocyanates of the formula II, in an inert solvent, such as ether or dichloromethane, can also be converted with phenol into the carbamates of the formula IV.

Carbamates of the formula VI are obtainable by known reactions or similarly to such reactions (for example EP-A 101 670), but can also be prepared from the corresponding isocyanates VII by reaction with phenol.

The isocyanates of the formula VII are obtained from the amines of the formula III by treatment with oxalyl chloride or phosgene (similarly to Angew. Chem. 83 (1971), 407 or EP-A 388 873).

The synthesis of 2-amino-4-fluoro-6-methoxypyrimidine and 2-amino-4-ethoxy-6-fluoropyrimidine is disclosed in DE-A-39 00 471.

2-Amino-4-chloro-6-trifluromethylpyrimidine is known from the literature (J. Heterocycl. Chem. 20 (1983), 219). The 4-alkoxy-2-amino-6-trifluoromethylpyrimidines III ($R^1$=methyl or ethyl; $R^2$=H) can be obtained from this intermediate by reaction with corresponding alcoholates (cf. process examples).

4-Methoxy-2-methylmercapto-6-trifluoropyrimidine (J. Heterocycl. Chem. 20 (1983), 219) can be converted with $H_2O_2$ into the 2-methylsulfone, which is reacted with amines and hydroxylamines to give the starting materials of the general formula III (cf. process examples).

The salts of the compounds I are obtainable in a conventional manner (EP-A-304 282 or U.S. Pat. No. 4,599,412). They are obtained by deprotonation of the corresponding sulfonylureas I in water or in an inert organic solvent at from −80° to 120° C., preferably from 0° to 60° C., in the presence of a base.

Examples of suitable bases are alkali metal or alkaline earth metal hydroxides, hydrides, oxides or alcoholates, such as sodium hydroxide, potassium hydroxide, lithium hydroxide, sodium methylate, sodium ethylate, sodium tert-butylate, sodium hydride, calcium hydride or calcium oxide.

Examples of suitable solvents in addition to water are alcohols, such as methanol, ethanol and tert-butanols, ethers, such as tetrahydrofuran and dioxane, acetonitrile, dimethylformamide, ketones, such as acetone and methyl ethyl ketone, and halohydrocarbons.

The deprotonation can be carried out at atmospheric pressure or at up to 50 bar, preferably at from atmospheric pressure to 5 bar gage pressure.

The compounds I or the herbicides containing them, and their environmentally compatible salts of alkali metals and alkaline earth metals, can very readily control weeds in crops such as wheat, rice and corn, without damaging the crops, an effect which occurs in particular at low application rates. They can be used, for example, in the form of directly sprayable solutions, powders, suspensions, including concentrated aqueous, oily or other suspensions or dispersions, emulsions, oil dispersions, pastes, dusts, broadcasting agents or granules, by spraying, nebulizing, dusting, broadcasting or pouring. The application forms depend on the intended uses; they should in any case ensure very fine distribution of the novel active ingredients.

The compounds I are suitable in general for the preparation of directly sprayable solutions, emulsions, pastes or oil dispersions. Suitable inert additives include mineral oil fractions having a medium to high boiling point, such as kerosene or diesel oil, and coal tar oils and oils of vegetable or animal origin, aliphatic, cyclic and aromatic hydrocarbons, eg. toluene, xylene, paraffin, tetrahydronaphthalene, alkylated naphthalenes or derivatives thereof, methanol, ethanol, propanol, butanol, cyclohexanol, cyclohexanone, chlorobenzene, isophorone or strong polar solvents, such as N,N-dimethylformamide, dimethyl sulfoxide, N-methylpyrrolidone or water.

Aqueous application forms can be prepared from emulsion concentrates, dispersions, pastes, wettable powders or water-dispersible granules by adding water. For the preparation of emulsions, pastes or oil dispersions, the substances, as such or dissolved in an oil or solvent, can be homogenized in water by means of wetting agents, adherents, dispersants or emulsifiers. However, concentrates which consist of active ingredient, wetting agents, adherents, dispersants or emulsifiers and possibly solvents or oil and which are suitable for dilution with water can also be prepared.

Suitable surfactants are the alkali metal, alkaline earth metal, ammoniumsalts of aromatic sulfonic acids, for example lignin-, phenol-, naphthalene- and dibutylnaphthalenesulfonic acid, and of fatty acids, alkyl- and alkylarylsulfonates, alkylsulfates, lauryl ether sulfates and fatty alcohol sulfates, and salts of sulfated hexa-, hepta- and octadecanols, and of fatty alcohol glycol ethers, condensates of sulfonated naphthalene and its derivates with formaldehyde, condensates of naphthalene and of naphthalenesulfonic acids with phenol and formaldehyde, polyoxyethylene octylphenol ether, ethoxylated isooctyl-, octyl- or nonylphenol, alkylphenol polyglycol ether, tributylphenyl polyglycol ether, alkylaryl polyether alcohols, isotridecyl alcohol, fatty alcohol/ethylene oxide condensates, ethoxylated castor oil, polyoxyethylene alkyl ether or polyoxypropylene, lauryl alcohol polyglycol ether acetal, sorbitol esters, ligninsulfite waste liquors or methylcellulose.

Powders, broadcasting agents and dusts can be prepared by mixing or milling the active ingredients together with a solid carrier.

Granules, for example coated, impregnated and homogeneous granules can be prepared by binding the active ingredients to solid carriers. Solid carriers are mineral acids, such as silicas, silica gels, silicates, talc, kaolin, limestone, lime, chalk, bole, loess, clay, dolomite, kieselguhr, calcium sulfate, magnesium sulfate, magnesium oxide, milled plastics, fertilizers, such as ammonium sulfate, ammonium phosphate, ammonium nitrate and ureas, and vegetable products, such as grain flour, bark meal, wood meal and nutshell meal, cellulosic powders or other solid carriers.

The formulations contain in general from 0.01 to 95, preferably from 0.5 to 90, % by weight of active ingredient. Examples of formulations are:

I. 90 parts by weight of compound No. 1 are mixed with 10 parts by weight of N-methyl-α-pyrrolidone, and a solution which is suitable for use in the form of small drops is obtained.

II. 20 parts by weight of compound No. 2 are dissolved in a mixture of 80 parts by weight of xylene, 10 parts by weight of the adduct of from 8 to 10 mol of ethylene oxide with 1 mol of N-monoethanololeamide, 5 parts by weight of the calcium salt of dodecylbenzenesulfonic acid and 5 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

III. 20 parts by weight of compound No. 7 are dissolved in a mixture which consists of 40 parts by weight of cyclohexanone, 30 parts by weight of isobutanol, 20 parts by weight of the adduct of 7 mol of ethylene oxide with 1 mol of isooctylphenol and 10 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

IV. 20 parts by weight of active ingredient No. 8 are dissolved in a mixture which consists of 25 parts by weight of cyclohexanone, 65 parts by weight of a mineral oil fraction boiling within a range from 210° to 280° C. and 10 parts by weight of the adduct of 40 mol of ethylene oxide with 1 mol of castor oil. By pouring the solution into 100,000 parts by weight of water and finely distributing it therein, an aqueous dispersion which contains 0.02% by weight of the active ingredient is obtained.

V. 20 parts by weight of active ingredient No. 14 are thoroughly mixed with 3 parts by weight of the sodium salt of diisobutylnaphthalene-α-sulfonic acid, 17 parts by weight of the sodium salt of a ligninsulfonic acid obtained from a sulfite waste liquor and 60 parts by weight of silica gel powder, and the mixture is milled in a hammer mill. By finely distributing the mixture in 20,000 parts by weight of water, a spray liquor which contains 0.1% by weight of the active ingredient is obtained.

VI. 3 parts by weight of active ingredient No. 27 are mixed with 97 parts by weight of finely divided kaolin.

A dust which contains 3% by weight of the active ingredient is obtained in this manner.

VII. 30 parts by weight of active ingredient No. 20 are thoroughly mixed with a mixture of 92 parts by weight of silica gel powder and 8 parts by weight of liquid paraffin, which was sprayed onto the surface of the silica gel. A preparation of the active ingredient having good adhesion is obtained in this manner.

VIII. 20 parts by weight of active ingredient No. 1 are thoroughly mixed with 2 parts by weight of the calcium salt of dodecylbenzenesulfonic acid, 8 parts by weight of a fatty alcohol polyglycol ether, 2 parts by weight of the sodium salt of a phenol/urea/formaldehyde condensate and 68 parts by weight of a paraffinic mineral oil. A stable oily dispersion is obtained.

Application may be effected by the preemergence or postemergence method. If the active ingredients are less well tolerated by certain crops, it is possible to use application methods in which the herbicides are sprayed with the aid of the sprayers in such a way that the leaves of the sensitive crops are as far as possible not affected, whereas the active ingredients reach the leaves of undesirable plants growing underneath or the uncovered soil surface (post-directed, lay-by).

The application rates of active ingredient are from 0.001 to 3, preferably from 0.01 to 1, kg/ha of active ingredient, depending on the aim of control, the season, the target plants and the stage of growth.

In view of the versatility of the application methods, the novel compounds or agents containing them may also be used in a further number of crops for eliminating undesirable plants. For example, the following crops are suitable:

| Botanical name | Common name |
|---|---|
| Allium cepa | onions |
| Ananas comosus | pineapples |
| Arachis hypogaea | peanuts (groundnuts) |
| Asparagus officinalis | asparagus |
| Beta vulgaris spp. altissima | sugarbeets |
| Beta vulgaris spp. rapa | fodder beets |
| Brassica napus var. napus | rapeseed |
| Brassica napus var. napobrassica | swedes |
| Brassica rapa var. silvestris | beets |
| Camellia sinensis | tea plants |
| Carthamus tinctorius | safflower |
| Citrus limon | lemons |
| Citrus sinensis | orange trees |
| Coffea arabica (Coffea canephora, Coffea liberica) | coffee plants |
| Cucumis sativus | cucumbers |
| Cynodon dactylon | Bermudagrass in turf and lawns |
| Daucus carota | carrots |
| Elaeis guineensis | oil palms |
| Fragaria vesca | strawberries |
| Glycine max | soy beans |
| Gossypium hirsutum (Gossypium arboreum Gossypium herbaceum Gossypium vitifolium) | cotton |
| Helianthus annuus | sunflowers |
| Hevea brasiliensis | rubber plants |
| Hordeum vulgare | barley |
| Humulus lupulus | hops |
| Ipomoea batatas | sweet potatoes |
| Juglans regia | walnut trees |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |

-continued

| Botanical name | Common name |
|---|---|
| Musa spp. | banana plants |
| Nicotiana tabacum (N. rustics) | tobacco |
| Olea europaea | olive trees |
| Oryza sativa | rice |
| Phaseolus lunatus | limabeans |
| Phaseolus vulgaris | snapbeans, green beans, dry beans |
| Picea abies | Norway spruce |
| Pinus spp. | pine trees |
| Pisum sativum | English peas |
| Prunus avium | cherry trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Solanum tuberosum | Irish potatoes |
| Sorghum bicolor (S. vulgare) | sorghum |
| Theobroma cacao | cacao plants |
| Trifolium pratense | red clover |
| Triticum aestivum | wheat |
| Triticum durum | durum wheat |
| Vicia faba | tick beans |
| Vitis vinifera | grapes |
| Zea mays | Indian corn, sweet corn, maize |

In order to broaden the action spectrum to achieve synergistic effects, the pyrimidinyl-substituted sulfonylureas of the formula I can be mixed and applied together with many members of other herbicidal or growth-regulating groups of active ingredients. For example, diazines, 4H-3,1-benzoxazine derivatives, benzothiadiazinones, 2,6-dinitroanilines, N-phenylcarbamates, thiocarbamates, halocarboxylic acids, triazines, amides, ureas, diphenyl ethers, triazinones, uracils, benzofuran derivatives, cyclohexane-1,3-dione derivatives, quinolinecarboxylic acid derivatives, phenoxy- and hetaryloxyphenylpropionic acids and their salts, esters and amides, and others, are suitable as components of the mixture.

It may also be useful to apply the compounds of the formula I, alone or in combination with other herbicides, also as a mixture together with further crop protection agents, for example with pesticides or agents for controlling phytopathogenic fungi or bacteria. The miscibility with mineral salt solutions which are used for eliminating nutrient and trace element deficiencies is also of interest. Nonphytotoxic oils and oil concentrates may also be added.

Typical examples of the preparation of the intermediates II–VII are given below.

1. 2-Amino-4-methoxy-6-trifluoromethylpyrimidine 28.1 g of a 30% strength by weight solution of sodium methylate (0.16 mol) in methanol (internal temperature below 40° C.) were added dropwise to a solution of 25.7 g of 2-amino-4-chloro-6-trifluoromethylpyrimidine (0.13 mol) in 200 ml of methanol. Stirring was carried out for one hour at 20°–25° C., the volatile components were removed under reduced pressure from a water pump at 65° C., the residue was taken up in 1 l of dichloromethane, the solution was washed with water, the dichloromethane phase was dried over $Na_2SO_4$ and the solvent was removed under reduced pressure from a water pump. 23.4 g of the product (93% of theory) were obtained as colorless crystals of melting point 108°–109° C.

2-Amino-4-ethoxy-6-trifluoromethylpyrimidine of melting point 114°–116° C. was obtained in a similar manner by reacting 2-amino-4-chloro-6-trifluoromethylpyrimidine with sodium methylate in ethanol.

2. 4-Methoxy-2-methylsulfonyl-6-trifluoromethylpyrimidine 7.1 g of a 30% strength by weight solution of (63 mmol) in water were added dropwise to a solution of 5.0 g of 2,4-methoxy-2-methylsulfonyl-6-trifluoromethylpyrimidine (22 mmol) in 50 ml of glacial acetic acid. The mixture was heated slowly to an internal temperature of 90° C. and stirred for 1 hour at this temperature, and the reaction batch was cooled to 25° C. and then introduced into 2 l of glacial acetic acid. The product was extracted with 200 ml of dichloromethane, the organic phase was washed with a dilute sodium thiosulfate solution and then with water, the solution of the product was dried over $Na_2SO_4$ and the solvent was removed under reduced prssure from a water pump. 5.1 g of the product (90% of theory) were obtained as colorless crystals of melting point 88°–90° C.

3. 2-(N-Methoxyamino)-4-methoxy-6-trifluoromethylpyrimidine 66.6 g of a 1.6 molar solution of n-butyllithium (0.156 mol) in n-hexane were added dropwise to a solution of 6.5 g of O-methylhydroxylammonium chloride (78 mmol) in 200 ml of tetrahydrofuran at –10° C. Stirring was carried out for 10 minutes at –10° C., and 20 g of 4-methoxy-2-methylsulfonyl-6-trifluoromethylpyrimidine (78 mmol) were added to the cloudy solution. Stirring was carried out for 1 hour at 25° C., the reaction batch was introduced into 200 ml of water, and the organic phase was separated off, washed with water and dried. Removal of the solvent gave an oily, slightly impure product, which could be crystallized in pentane at –78° C. 7.5 g of the product (43% of theory) were obtained as colorless crystals of melting point. 44°–46° C.

4. 2-Isocyanato-4-methoxy-6-trifluoromethylpyrimidine 38.3 g of oxalyl chloride (0.3 mol) were added dropwise to a suspension of 2-amino-4-methoxy-6-trifluoromethylpyrimidine (78 mmol) in 100 ml of toluene. The refluxing mixture was stirred for 4 hours, after which the homogeneous solution obtained was subjected to fractional distillation. The title compound (9.9 g; 58% of theory) was obtained as an oil of boiling point 44°–50° C. (0.5 mbar).

5. 4-Methoxy-2-[(phenoxycarbonyl)amino]-6-trifluoromethylpyrimidine 4.2 g of phenol (45 mmol) were added at 25° C. to a solution of 9.9 g of 2-isocyanato-4-methoxy-6-trifluoromethylpyrimidine (45 mmol) in 50 ml of methylene chloride. Stirring was carried out for 16 hours at 25° C., the methylene chloride was distilled off under reduced pressure and the residue was stirred vigorously with 100 ml of a diisopropyl ether/hexane mixture (v/v 1:20), whereupon crystallization occurred. The product was filtered off with suction and dried under reduced pressure from a water pump at 50° C. The title compound (12.2 g; 87% of theory) was obtained as colorless crystals of melting point 85°–88° C.

6. 2-(Methylsulfinyl)benzenesulfonamide 14.8 g of hydrogen peroxide (0.13 mol), 30% strength in $H_2O$, were added dropwise at from 25° to 30° C. to a suspension of 26.5 g 6f 2-(methylthio)benzenesulfonamide (0.13 mol) and 2.1 g of $Na_2WO_4 \cdot 2H_2O$ in 88 ml of glacial acetic acid. Stirring was carried out for 45 minutes at 25° C., the reaction mixture was poured onto 400 ml of water and the precipitate was filtered off with suction. It was washed with water and dried under reduced pressure from a water pump at 40° C. 24.3 g (85% of theory) of the title compound were thus obtained.

$^1$H-NMR spectrum (250 MHz, $CD_3SOCD_3$, int. TMS): 8.16 d (1H), 7.82–8.0 m (2H), 7.77 br (2H), 7.63–7.85 m (2H), 2.76 s (3H).

7. N-(n-Butylamino)carbonyl-2-methylsulfinylbenzenesulfonamide 10.2 g of n-Butyl isocyanate (0.10 mol) were added dropwise at 25° C. to a suspension of 20.1 g of 2-(methylsulfinyl)benzenesulfonamide (0.09 mol) in 250 ml of acetonitrile. 13.9 g of potassium carbonate (0.10 mol) were added, after which the refluxing mixture was stirred for 4 hours. After cooling to 0° C., the mixture was poured onto 400 ml ice/water, brought to a pH of 1 by adding concentrated hydrochloric acid and extracted with methylene chloride. The organic extracts were washed neutral with water and dried. After removal of the solvent, 25 g of the title compound (85% of theory) were obtained as a pale brown oil.

$^1$H-NMR spectrum (250 MHz, $CDCl_3$, int. TMS): 8.28 d (1H), 8.20 d (1H), 7.89 t (2H), 7.73 t (1H), 6.03 t (1H), 3.13 m (2H), 2.95 s (3H), 1.38 m (2H), 1.24 m (2H), 0.85 t (3H).

8. 2-(Methylsuliinyl)benzenesulfonyl isocyanate

Phosgene was slowly passed into a refluxing solution (cooled with solid carbon dioxide) of 25 g of N-[(n-butylamino)carbonyl-2-methylsulfinyl]benzenesulfonamide and 0.4 g of 1,4-diazabicyclo[2.2.2]octane in 400 ml of xylene, until an internal temperature of 110° C. was reached. The cooling was removed and the volatile components were distilled off under reduced pressure from a water pump at 80° C. The remaining sulfonyl isocyanate was reacted without further purification.

9. N-[(n-Butylamino)carbonyl-2-(N,N-dimethylaminosulfonyl)]benzenesulfonamide 18.6 g of n-butyl isocyanate (0.18 mol) were added dropwise at 25° C. to a suspension of 44.2 g of 2-[N,N-dimethylaminosulfonyl]benzenesulfonamide (0.17 mol) (prepared similarly to 2-[N,N-diethylamino)-sulfonyl]benzenesulfonamide in U.S. Pat. No. 4,310,346) in 450 ml of acetonitrile. After the addition of 25.4 g of potassium carbonate (0.18 mol), the refluxing mixture was stirred for 3 hours. After cooling to 0° C., the reaction mixture was poured onto 400 ml of ice/water and brought to a pH of 1 by adding concentrated hydrochloric acid, and the precipitate formed was filtered off with suction, washed neutral with water and dried under reduced pressure from a water pump at 40° C. 60 g of the title compound (99% of theory) were obtained in this manner.

$^1$H-NMR spectrum (250 MHz, $CDCl_3$ int. TMS): 8.55 br (1H), 8.30 d (1H), 8.05 d (1H), 7.7–7.9 m (1H), 6.52 t (1H), 3.17 qua (2H), 2.94 s (6H), 1.43 qui (2H), 1.25 sext (2H), 0.85 t (3H).

10. 2-[N,N-(Dimethylamino)sulfonyl]benzenesulfonyl isocyanate

The sulfonylurea obtained in Example 9. was converted into the corresponding sulfonyl isocyanate, similarly to the preparation of 2-(methylsulfinyl)benzenesulfonyl isocyanate.

Typical examples of the synthesis of the sulfonylureas I and their salts are described below.

11. 2-Nitro-1-N-[4-methoxy-6-trifluoromethylpyrimidine-2-yl)aminocarbonyl]benzenesulfonamide 8 g of 2-nitrobenzenesulfonyl isocyanate (35 mmol) in 10 ml of 1,2-dichloroethane were added at 25° C. to a mixture of 6.7 g of 2-amino-4-methoxy-6-trifluoromethylpyrimidine (35 mmol) in 10 ml of dichloromethane. Stirring was carried out for 14 hours at 25° C., after which the solvent was removed under reduced pressure from a water pump at 40° C. and the residue was stirred vigorously for 2 hours with 50 ml of diethyl ether. The product was filtered off with suction and dried under reduced pressure from a water pump at 40° C. 3 g of the title compound (20% of theory) were obtained as colorless crystals of melting point 204°–205° C.

12. Sodium 2-nitro-1-N-[(4-methoxy-6-trifluoromethylpyrimidin-2-yl)aminocarbonyl]benzenesulfonamide 0.65 g (3.6 mmol) of a solution of sodium methylate (30% by weight) in methanol was added at 25° C. to a suspension of 1.5 g of 2-nitro-1-N-[(4-methoxy-6-trifluoromethylpyrimidin-2-yl)aminocarbonyl]benznenesulfonamide (3.6 mmol) in 20 ml of methanol. Stirring was carried out for 10 minutes at 25° C. after which the homogeneous solution was evaporated down under reduced pressure from a water pump at 50° C. The title compound was obtained in quantitative yield as colorless crystals having a decomposition temperature of 164°–166° C.

13. 2-[[(4-Fluoro-6-methoxypyrimidin-2-yl)aminocarbonyl]aminosulfonyl]benzenesulfonic acid N,N-dimethylamide 8.1 g of 2-(dimethylamino)sulfonylbenzenesulfonyl isocyanate (28 mmol) were added at 25° C. to a suspension of 4.0 g of 2-amino-4-fluoro-6-methoxypyrimidine (28 mmol) in 30 ml of methylene chloride. Stirring was carried out for 16 hours at 25° C. and the precipitated product was filtered off with suction. To eliminate unconverted pyrimidine, the precipitate was stirred vigorously with diisopropyl ether. The product was filtered off with suction, washed with n-hexane and dried at 40° C. under reduced pressure from a water pump.

7.2 g (59%) of the title compound (decomposition temperature 198° C.) were obtained in this manner. Further product could be isolated from the mother liquor.

$^1$H-NMR spectrum (250 MHz, $CD_3COCD_3$, int. TMS, δ (ppm)): 2.91 s (6H), 4.17 s (6H), 6.24 s (1H), 7.8–8.0 m (2H), 8.04 m (1H), 8.50 m (1H), 9.63 br (1H), 12.25 br (1H).

14. [(4-Fluoro-6-methoxypyrimidine-2-yl)aminocarbonyl]-2-methylsulfonylbenzenesulfonamide 4.7 g of 2-(methylsulfinyl)benzenesulfonyl isocyanate (19 mmol) were added at 25° C. to a solution of 2.7 g of 2-amino-4-fluoro-6-methoxypyrimidine (19 mmol) in 30 ml of methylene chloride. Stirring was carried out for 16 hours at 25° C., after which the precipitated product was filtered off with suction, washed with a little ether and dried under reduced pressure from a water pump at 50° C. 0.9 g of the title compound (10% of theory) at melting point 161°–176° C. was obtained in this manner. Further product could be isolated from the mother liquor.

The active ingredients stated in Table 1 below were obtained by a similar preparation method.

TABLE 1

| Active Ingredient No. | $R^1$ | $R^3$ | $R^4$ | $R^5$ | M.p. [°C.] |
|---|---|---|---|---|---|
| 1 | $CH_3$ | $SO_2N(CH_3)_2$ | H | F | 198 |
| 2 | $CH_3$ | $SO_2N(CH_3)_2$ | H | F | 161–168* |
| 3 | $CH_3$ | $SO_2N(CH_3)_2$ | H | F | 184–192** |
| 4 | $CH_3$ | $OCF_2CF_2H$ | H | F | 135–139 |
| 5 | $CH_3$ | $OCF_3$ | H | F | 181–182 |
| 6 | $CH_3$ | $OCF_3$ | H | F | 140–146* |
| 7 | $CH_3$ | $NO_2$ | H | F | 159–167 |
| 8 | $CH_3$ | $NO_2$ | H | F | 214* |
| 9 | $CH_3$ | $SO_2(C_2H_5)_2$ | H | F | 206 |
| 10 | $CH_3$ | $SO_2(C_2H_5)_2$ | H | F | 200* |

TABLE 1-continued

| Active Ingredient No. | $R^1$ | $R^3$ | $R^4$ | $R^5$ | M.p. [°C.] |
|---|---|---|---|---|---|
| 11 | $CH_3$ | $CF_3$ | H | F | 181 |
| 12 | $CH_3$ | $CF_3$ | H | F | 178* |
| 13 | $CH_3$ | $CH_3$ | H | F | 185–193 decomp. |
| 14 | $CH_3$ | $CH_3$ | H | F | 166* |
| 15 | $CH_3$ | $OCH_3$ | H | F | 207–209 |
| 16 | $CH_3$ | $OCH_3$ | H | F | 170* |
| 17 | $CH_3$ | $CF_3$ | 6-$CH_3$ | F | 206–209 decomp. |
| 18 | $CH_3$ | $CF_3$ | 6-$CH_3$ | F | >250* |
| 19 | $CH_3$ | $NO_2$ | H | $CF_3$ | 204–205 |
| 20 | $CH_3$ | $NO_2$ | H | $CF_3$ | 164–166 |
| 21 | $CH_3$ | $CF_3$ | H | $CF_3$ | 194–196 |
| 22 | $CH_3$ | $CF_3$ | H | $CF_3$ | 174–179* |
| 23 | $CH_3$ | $CF_3$ | H | $CF_3$ | 156–160** |
| 24 | $CH_3$ | $SO_2CH_3$ | H | $CF_3$ | 202–204 |
| 25 | $CH_3$ | $OSO_2CH_3$ | H | $CF_3$ | 197–200 |
| 26 | $CH_3$ | $OCF_2CF_2H$ | H | F | 164* |
| 27 | $CH_3$ | $SCH_3$ | H | F | 192–193 |
| 28 | $CH_3$ | $SCH_3$ | H | F | 120–135* |
| 29 | $CH_3$ | $SCH_3$ | H | F | 205–210** |
| 30 | $CH_3$ | $CH_2OCH_3$ | H | F | 167–169 |
| 31 | $CH_3$ | $SCH_3$ | H | $CF_3$ | 163–166 |
| 32 | $CH_3$ | $SCH_3$ | H | $CF_3$ | 146–151* |
| 33 | $C_2H_5$ | $SCH_3$ | H | $CF_3$ | 172–173 |
| 34 | $CH_3$ | $CH_2OCH_3$ | H | $CF_3$ | 165 |
| 35 | $CH_3$ | $OCF_3$ | H | $CF_3$ | 153–154 |
| 36 | $CH_3$ | $OCF_3$ | H | $CF_3$ | 107* |
| 37 | $CH_3$ | $SCH_3$ | 6-$SCH_3$ | $CF_3$ | 190–192 |
| 38 | $CH_3$ | $SCH_3$ | 6-$SCH_3$ | $CF_3$ | 174* |
| 39 | $CH_3$ | $SCH_3$ | 6-$SCH_3$ | F | 191–193 |
| 40 | $CH_3$ | $SCH_3$ | 6-$SCH_3$ | F | 186* |
| 41 | $CH_3$ | $OCH_2CF_3$ | 5-$OCH_2CF_3$ | F | 189–190 |
| 42 | $CH_3$ | $OCH_2CF_3$ | 5-$OCH_2CF_3$ | F | 152* decomp. |
| 43 | $CH_3$ | $SO_2C_2H_5$ | 5-Cl | F | 205–209 decomp. |

*Na salt (decomp.)
**K salt (decomp.)

The compounds shown below can also be obtained in a similar manner:

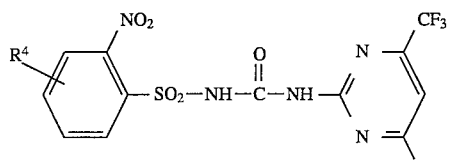

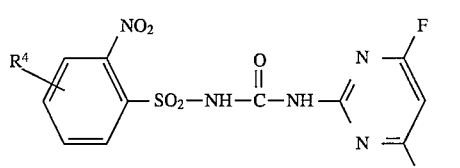

or the Na salts thereof, where $R^4$ is hydrogen, 3-methyl, 4-methyl, 5-methyl, 6-methyl, 3-ethyl, 4-ethyl, 5-ethyl, 6-ethyl, 3-fluoro, 4-fluoro, 5-fluoro, 6-fluoro, 3-chloro, 4-chloro, 5-chloro, 6-chloro, 3-methoxy, 4-methoxy, 5-methoxy, 6-methoxy, 3-ethoxy, 4-ethoxy, 5-ethoxy, 6-ethoxy or 6-methylthio;

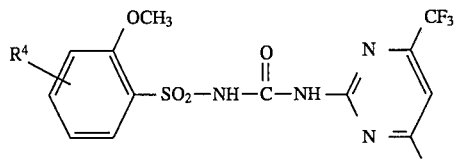

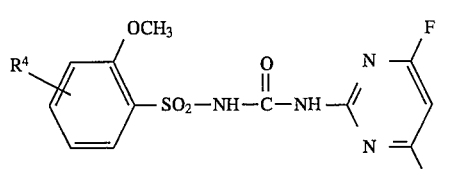

or the Na salts thereof, where $R^4$ is hydrogen, 3-methyl, 4-methyl, 5-methyl, 6-methyl, 3-ethyl, 4-ethyl, 5-ethyl, 6-ethyl, 3-fluoro, 4-fluoro, 5-fluoro, 6-fluoro, 3-chloro, 4-chloro, 5-chloro, 6-chloro, 3-methoxy, 4-methoxy, 5-methoxy, 6-methoxy, 3-ethoxy, 4-ethoxy, 5-ethoxy, 6-ethoxy or 6-methylthio;

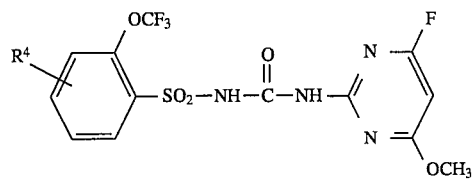

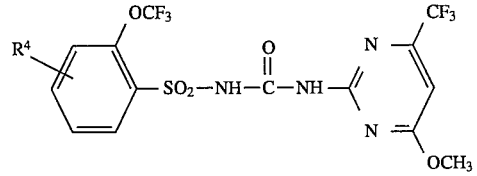

or the Na salts thereof, where $R^4$ is hydrogen, 3-methyl, 4methyl, 5-methyl, 6-methyl, 3-ethyl, 4-ethyl, 5-ethyl, 6-ethyl, 3-fluoro, 4-fluoro, 5-fluoro, 6-fluoro, 3-chloro, 4-chloro, 5-chloro, 6-chloro, 3-methoxy, 4-methoxy, 5-methoxy, 6-methoxy, 3-ethoxy, 4-ethoxy, 5-ethoxy, 6-ethoxy or 6-methylthio;

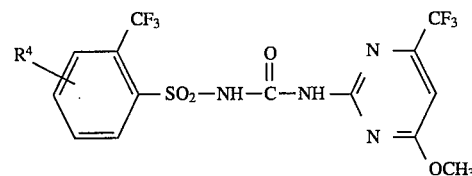

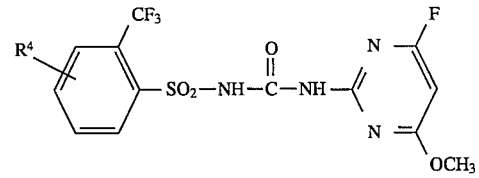

or the Na salts thereof, where $R^4$ is hydrogen, 3-methyl, 4-methyl, 5-methyl, 6-methyl, 3-ethyl, 4-ethyl, 5-ethyl, 6-ethyl, 3-fluoro, 4-fluoro, 5-fluoro, 6-fluoro, 3-chloro, 4-chloro, 5-chloro, 6-chloro, 3-methoxy, 4-methoxy, 5-methoxy, 6-methoxy, 3-ethoxy, 4-ethoxy, 5-ethoxy, 6-ethoxy or 6-methylthio;

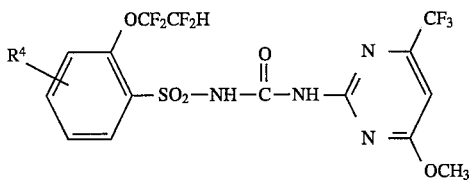

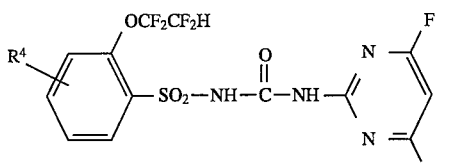

or the Na salts thereof, where $R^4$ is hydrogen, 3-methyl, 4-methyl, 5-methyl, 6-methyl, 3-ethyl, 4-ethyl, 5-ethyl, 6-ethyl, 3-fluoro, 4-fluoro, 5-fluoro, 6-fluoro, 3-chloro, 4-chloro, 5-chloro, 6-chloro, 3-methoxy, 4-methoxy, 5-methoxy, 6-methoxy, 3-ethoxy, 4-ethoxy, 5-ethoxy, 6-ethoxy or 6-methylthio;

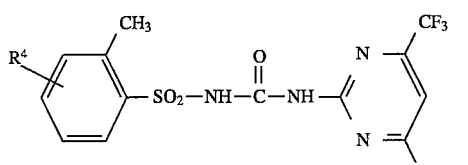

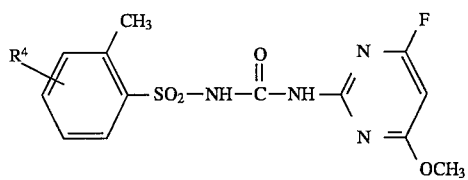

or the Na salts thereof, where $R^4$ is hydrogen, 3-methyl, 4-methyl, 5-methyl, 6-methyl, 3-ethyl, 4-ethyl, 5-ethyl, 6-ethyl, 3-fluoro, 4-fluoro, 5-fluoro, 6-fluoro, 3-chloro, 4-chloro, 5-chloro, 6-chloro, 3-methoxy, 4-methoxy, 5-methoxy, 6-methoxy, 3-ethoxy, 4-ethoxy, 5-ethoxy, 6-ethoxy or 6-methylthio;
or the Na salts thereof, where $R^3$ is hydrogen, 3-methyl, 4-methyl, 5-methyl, 6-methyl, 3-ethyl, 4-ethyl, 5-ethyl, 6-ethyl, 3-fluoro, 4-fluoro, 5-fluoro, 6-fluoro, 3-chloro, 4-chloro, 5-chloro, 6-chloro, 3-methoxy, 4-methoxy, 5-methoxy, 6-methoxy, 3-ethoxy, 4-ethoxy, 5-ethoxy, 6-ethoxy or 6-methylthio;

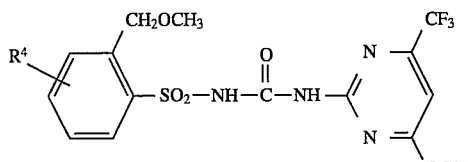

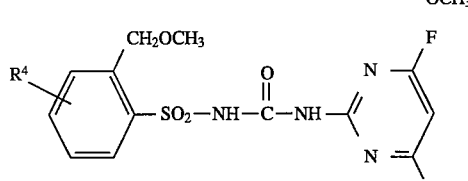

or the Na salts thereof, where $R^4$ is hydrogen, 3-methyl, 4-methyl, 5-methyl, 6-methyl, 3-ethyl, 4-ethyl, 5-ethyl, 6-ethyl, 3-fluoro, 4-fluoro, 5-fluoro, 6-fluoro, 3-chloro, 4-chloro, 5-chloro, 6-chloro, 3-methoxy, 4-methoxy, 5-methoxy, 6-methoxy, 3-ethoxy, 4-ethoxy, 5-ethoxy, 6-ethoxy or 6-methylthio;

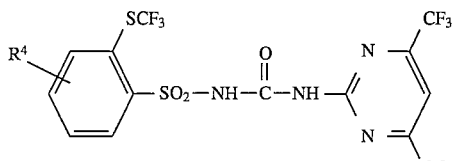

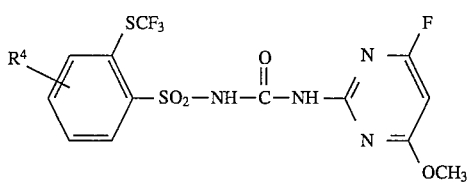

or the Na salts thereof, where $R^4$ is hydrogen, 3-methyl, 4-methyl, 5-methyl, 6-methyl, 3-ethyl, 4-ethyl, 5-ethyl, 6-ethyl, 3-fluoro, 4-fluoro, 5-fluoro, 6-fluoro, 3-chloro, 4-chloro, 5-chloro, 6-chloro, 3-methoxy, 4-methoxy, 5-methoxy, 6-methoxy, 3-ethoxy, 4-ethoxy, 5-ethoxy, 6-ethoxy or 6-methylthio;

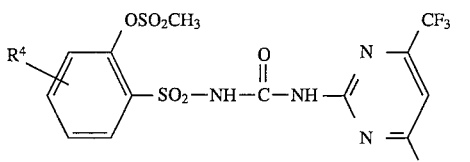

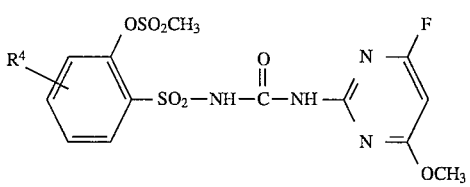

or the Na salts thereof, where $R^4$ is hydrogen, 3-methyl, 4-methyl, 5-methyl, 6-methyl, 3-ethyl, 4-ethyl, 5-ethyl, 6-ethyl, 3-fluoro, 4-fluoro, 5-fluoro, 6-fluoro, 3-chloro, 4-chloro, 5-chloro, 6-chloro, 3-methoxy, 4-methoxy, 5-methoxy, 6-methoxy, 3-ethoxy, 4-ethoxy, 5-ethoxy, 6-ethoxy or 6-methylthio;

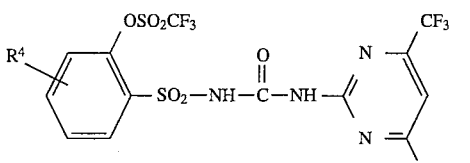

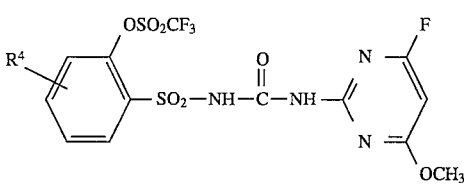

or the Na salts thereof, where $R^4$ is hydrogen, 3-methyl, 4-methyl, 5-methyl, 6-methyl, 3-ethyl, 4-ethyl, 5-ethyl, 6-ethyl, 3-fluoro, 4-fluoro, 5-fluoro, 6-fluoro, 3-chloro, 4-chloro, 5-chloro, 6-chloro, 3-methoxy, 4-methoxy, 5-methoxy, 6-methoxy, 3-ethoxy, 4-ethoxy, 5-ethoxy, 6-ethoxy or 6-methylthio.

USE EXAMPLES

The herbicidal action of the N-[(pyrimidin-2-yl)aminocarbonyl]benzenesulfonamide of the formula I on the growth of the test plants is demonstrated by the following greenhouse experiments.

The culture vessels used are plastic flower pots having a capacity of 300 cm$^3$ and containing loamy sand with about 3.0% of humus as a substrate. The seeds of the test plants are sown shallow and separately according to species.

For the purpose of the postemergence treatment, the plants which are either directly sown or grown in the same vessels are selected, or they are first grown separately as seedlings and transplanted into the test vessels a few days before the treatment.

The test plants, at a height of growth of from 3 to 15 cm, depending on the form of growth, are then treated with the active ingredients which are suspended or emulsified in water as a distributing. medium and which are sprayed through finely distributing nozzles. The application rate for the postemergence treatment is 0.06 and 0.03 kg/ha a.i. (active ingredient).

The test vessels are placed in a greenhouse, warmer areas (from 20° to 35° C.) being preferred for warmth-loving species and from 10° to 20° C. being preferred for those of temperate climates. The test period extends over from 2 to 4 weeks. During this time, the plants are tended and their reaction to the individual treatments is evaluated.

Evaluation is based on a scale of from 0 to 100. 100 means no emergence of the plants or complete destruction of at least the above-ground parts, and 0 means no damage or normal course of growth.

The plants used in the greenhouse experiments consisted of the following species:

| Botanical name | Common name |
| --- | --- |
| Alopecurus myosuroides | slender foxtail |
| Echinochloa crus-galli | barnyard grass |
| Setaria italica | foxtail millet |
| Zea mays | corn |

When used at a rate of 0.06 and 0.03 kg/ha a.i. by the postemergence method, Example No. 11 controls undesirable plants verywell while at the same time being compatible with the example crop corn.

Compound No. 11 was compared with the comparative substance J disclosed in EP-A 101 308. The results, which are listed in Table I, demonstrate the substantially better herbicidal activity in conjunction with high selectivity in the example crop corn.

Compounds No. 23, 25 and 19 were compared with the comparative substances N and O disclosed in DE-A 27 15 786 (U.S. Pat. No. 4,120,691). The results listed in Tables II to IV demonstrate the better herbicidal activity in conjunction with high selectivity in the example crop winter wheat (Triticum aestivum).

TABLE I

Herbicidal activity in postemergence application in the greenhouse

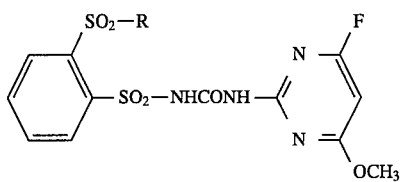

| Example No. | 11 | | J | |
|---|---|---|---|---|
| R | $C_2H_5$ | | $n\text{-}C_3H_7$ | |
| Application rate (kg/ha a.i.) | 0.06 | 0.03 | 0.06 | 0.03 |
| Test plants (damage in %) | | | | |
| Alopecurus myosuroides | 95 | 80 | 55 | 0 |
| Echinochloa crus-galli | 100 | 98 | 30 | 10 |
| Setaria italica | 85 | 85 | 20 | 15 |
| Zea mays | 15 | 15 | 10 | 0 |

TABLE II

Herbicidal activity in postemergence application in the greenhouse

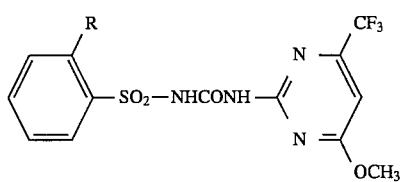

| Example No. | 25 | | N | |
|---|---|---|---|---|
| R | $OSO_2CH_3$ | | Cl | |
| Application rate (kg/ha a.i.) | 0.06 | 0.03 | 0.06 | 0.03 |
| Test plants (damage in %) | | | | |
| Triticum aestivum | 20 | 0 | 10 | 5 |
| Echinochloa crus-galli | 85 | 70 | 40 | 30 |
| Amaranthus retroflexus | 100 | 100 | 98 | 98 |
| Sinapis alba | 100 | 100 | 90 | 80 |
| Solanum nigrum | 100 | 100 | 40 | 30 |
| Veronica spp. | 85 | 75 | 40 | 30 |

TABLE III

Herbicidal activity in postemergence application in the greenhouse

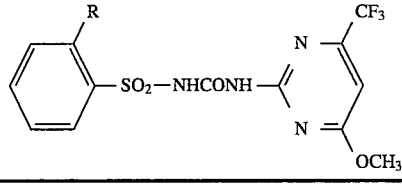

| Example No. | 23 | | N | |
|---|---|---|---|---|
| R | $CF_3$ | | Cl | |
| Application rate (kg/ha a.i.) | 0.06 | 0.03 | 0.06 | 0.03 |
| Test plants (damage in %) | | | | |
| Echinochloa crus-galli | 88 | 60 | 40 | 30 |
| Abutilon theoprasti | 95 | 95 | 50 | 40 |
| Chenopodium album | 100 | 100 | 95 | 90 |
| Chrysanthenum corinarium | 100 | 100 | 75 | 65 |

TABLE III-continued

Herbicidal activity in postemergence application in the greenhouse

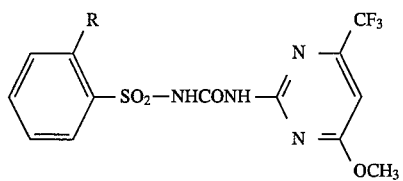

| Galium aparine | 90 | 90 | 40 | 20 |
|---|---|---|---|---|
| Solanum nigrum | 100 | 100 | 40 | 30 |
| Polygonum persicaria | 100 | 95 | 80 | 50 |

TABLE IV

Herbicidal activity in postemergence application in the greenhouse

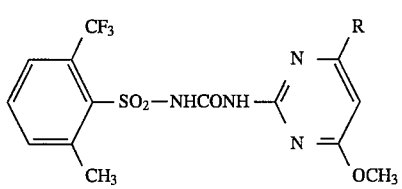

| Example No. | 19 | | O | |
|---|---|---|---|---|
| R | F | | Cl | |
| Application rate (kg/ha a.i.) | 0.06 | 0.03 | 0.06 | 0.03 |
| Test plants (damage in %) | | | | |
| Triticum aestivum | 10 | 10 | 50 | 40 |
| Echinochloa crus-galli | 75 | 65 | 80 | 80 |
| Amaranthus retroflexus | 100 | 100 | 100 | 100 |
| Sinapis alba | 75 | 75 | 90 | 90 |
| Solanum nigrum | 100 | 95 | 98 | 90 |

We claim:

1. An N-[(pyrimidin-2-yl)aminocarbonyl]benzenesulfonamide of the formula I

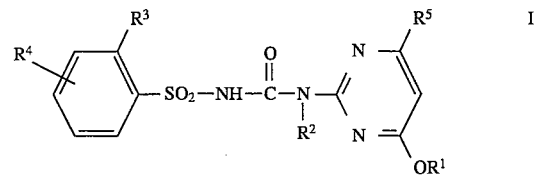

where $R^1$ is methyl;

$R^2$ is hydrogen;

$R^3$ is $C_1$–$C_4$-alkyl which carries from one to three methoxy groups or fluorine atoms;

or $R^3$ is a group $ER^6$ in which E is O or S, $R^6$ being $C_1$–$C_2$-alkyl, which may carry from 1 to 3 or 1 to 5 fluorine atoms, with the exception of difluoromethoxy, and, if E is O and at the same time $R^5$ is trifluoromethyl, $R^6$ may furthermore be methylsulfonyl, ethylsulfonyl, trifluoromethylsulfonyl, allylsulfonyl or propargylsulfonyl;

or $R^3$ is di-$C_1$–$C_3$-alkylaminosulfonyl if $R^5$ is fluorine;

or $R^3$ is $C_1$ or $C_2$-alkylsulfonyl which may carry 1–3 halogen atoms;

$R^4$ is hydrogen, methyl, ethyl, methoxy, ethoxy, fluorine, chlorine, methylthio, ethylthio or $C_1$–$C_2$-haloalkoxy;

and $R^5$ is fluorine or trifluoromethyl, and its environmentally compatible salts.

2. An N-[(pyrimidin-2-yl)aminocarbonyl]benzenesulfonamide of the formula I as defined in claim 1, where $R^1$ is methyl, $R^2$ and $R^4$ are hydrogen, $R^3$ is methylsulfonyloxy (E=O, $R^6$=methylsulfonyl) and $R^5$ is trifluoromethyl.

3. An N-[(pyrimidin-2-yl)aminocarbonyl]benzenesulfonamide of the formula I as defined in claim 1, where $R^1$ is methyl, $R^2$ and $R^4$ are hydrogen, $R^3$ is trifluoromethyl and $R^5$ is trifluoromethyl or fluorine.

4. An N-[(pyrimidin-2-yl)aminocarbonyl]benzenesulfonamide of the formula I as defined in claim 1, where $R^1$ is methyl, $R^2$ and $R^4$ are hydrogen, $R^3$ is trifluoromethoxy and $R^5$ is trifluoromethyl or fluorine.

5. An N-[(pyrimidin-2-yl)aminocarbonyl]benzenesulfonamide of the formula I as defined in claim 1, where $R^1$ is methyl, $R^2$ is hydrogen, $R^3$ is thiomethyl or methoxy, $R^4$ is 6-thiomethyl and $R^5$ is trifluoromethyl or fluorine.

6. An N-[(pyrimidin-2-yl)aminocarbonyl]benzenesulfonamide of the formula I as defined in claim 1, where $R^1$ is methyl, $R^2$ and $R^4$ are hydrogen, $R^3$ is methoxymethyl and $R^5$ is trifluoromethyl or fluorine.

7. An N-[(pyrimidin-2-yl)aminocarbonyl]benzenesulfonamide of the formula I as defined in claim 1, where $R^1$ is methyl, $R^2$ and $R^4$ are hydrogen, $R^3$ is nitro and $R^5$ is trifluoromethyl or fluorine.

8. An N-[(pyrimidin-2-yl)aminocarbonyl]benzenesulfonamide of the formula I as defined in claim 1, where $R^1$ is methyl, $R^2$ and $R^4$ are hydrogen, $R^3$ ethylsulfonyl and $R^5$ is trifluoromethyl or fluorine.

9. An N-[(pyrimidin-2-yl)aminocarbonyl]benzenesulfonamide of the formula I as defined in claim 1, where $R^1$ is methyl, $R^2$ and $R^4$ are hydrogen, $R^3$ is N,N-dimethylsulfamoyl and $R^5$ is fluorine.

10. The compound of claim 1 which is

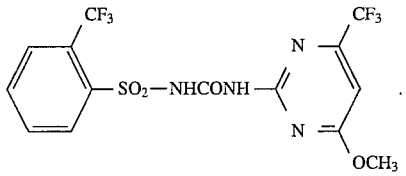

11. The compound of claim 1 which is

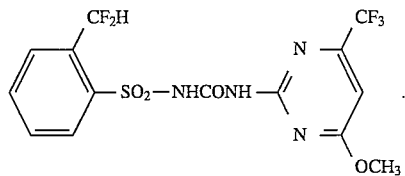

12. The compound of claim 1 which is

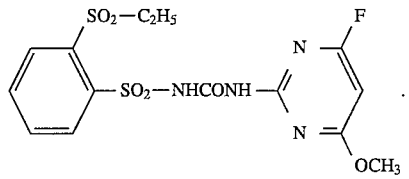

13. The compound of claim 1 which is

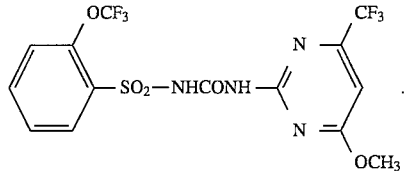

14. A herbicidal composition containing an effective amount of an N-[(pyrimidin-2-yl)aminocarbonyl]benzenesulfonamide of the formula I as defined in claim 1 or its salt and conventional carriers.

15. A method for controlling undesirable plant growth, wherein a herbicidal amount of an N-[(pyrimidin-2-yl)amminocarbonyl]benzenesulfonamide of the formula I as defined in claim 1 or of one of its salts is allowed to act on the plants or their habitat.

* * * * *